US007999690B1

(12) United States Patent
Shilts

(10) Patent No.: US 7,999,690 B1
(45) Date of Patent: Aug. 16, 2011

(54) DOOR EXCESS WEIGHT ALARM

(76) Inventor: Steven Shilts, San Diego, CA (US)

( * ) Notice: Subject to any disclaimer, the term of this patent is extended or adjusted under 35 U.S.C. 154(b) by 413 days.

(21) Appl. No.: 12/247,061

(22) Filed: Oct. 7, 2008

Related U.S. Application Data

(60) Provisional application No. 60/997,966, filed on Oct. 9, 2007.

(51) Int. Cl.
*G08B 21/00* (2006.01)
*A61B 5/11* (2006.01)
*H01H 3/14* (2006.01)

(52) U.S. Cl. ...................................... 340/666; 200/85 R

(58) Field of Classification Search ................ 200/85 R; 73/768, 774; 340/666, 665, 540, 545.2, 825.19, 340/573.1
See application file for complete search history.

(56) References Cited

U.S. PATENT DOCUMENTS 4,228,426 A 10/1980 Roberts
4,551,713 A 11/1985 Aossey
4,675,659 A 6/1987 Jenkins, Jr. et al.
4,920,241 A * 4/1990 Miller ......................... 200/86 R
4,924,214 A 5/1990 Hill
5,066,835 A * 11/1991 Miller et al. ............... 200/61.43
6,396,010 B1 * 5/2002 Woodward et al. ........ 200/61.43
7,024,823 B2 4/2006 Keller
7,466,237 B1 12/2008 Cook
2008/0061969 A1 * 3/2008 Okude et al. .................. 340/541

* cited by examiner

*Primary Examiner* — Jennifer Mehmood

(74) *Attorney, Agent, or Firm* — QuickPatents, Inc.; Kevin Prince

(57) ABSTRACT

A weight alarm system for indicating excess weight applied to a door is disclosed. The alarm system comprises an excess weight sensing means, such as a pressure strip means fixed around a peripheral edge of the door or a load cell fixed between the peripheral edge of the door and a structural mount for the door. A door latching mechanism includes traverses either a front or a rear side of the door and includes a latching bolt. When the excess weight sensing means if actuated a signaling means is activated to alert those nearby to a possible suicide attempt.

17 Claims, 7 Drawing Sheets

DOOR EXCESS WEIGHT ALARM

CROSS-REFERENCE TO RELATED APPLICATIONS

This application claims the benefit of U.S. Provisional Patent Application 60/997,966, filed on Oct. 9, 2007, and incorporated herein by reference.

STATEMENT REGARDING FEDERALLY SPONSORED RESEARCH AND DEVELOPMENT

Not Applicable.

FIELD OF THE INVENTION

This invention relates to alarm sensors, and more particularly to a door having a weight sensor for sounding an alarm.

DISCUSSION OF RELATED ART

In healthcare facilities, a variety of patient activity monitoring devices are being used for preventing a patient from indulging in any self-harming activities. Alarm devices with a nurse call system have been used for alerting a nurse or other attendant in case of an emergency.

One prior art device, taught in U.S. Pat. No. 6,166,644 issued to Stroda on Dec. 26, 2000 provides a patient monitoring device that includes sensors and signaling components. An alligator clip is fastened to the patient by a cord that is connected to a switch so as to monitor a patient. The device is activated when the patient moves beyond the length of the cord. A pressure pad is located under the patient and armed by an application of the weight to the pad. Upon removal of the weight, the alarm is sounded. However, this device fails to monitor the patient's attempt for committing suicide, particularly by hanging on a door.

U.S. Pat. No. 5,844,488 issued to Musick on Dec. 1, 1998 provides a bed sensor and an alarm with a fall-prevention monitoring system. When a patient moves toward either edge of a bed, an edge switch is activated which generates an early warning signal indicating the attending personnel that a patient has moved from the center of the bed to an edge and may be attempting to exit the bed. This early warning signal provides time for an attendant to reach the patient before he or she has actually evacuated the bed. This system is complex, expensive and difficult to operate, and not suitable for implementation with a door.

U.S. Pat. No. 5,751,214 issued to Cowley on May 12, 1998 discloses a multi-purpose device for monitoring patient movement in a number of different ways. The device includes a data processor programmed to respond to signals from multiple external sensors that easily connect to the device through a jack in the device housing. If movement of the patient beyond a limit is sensed, the device generates an alarm for an attendant. To sense the different types of patient movement, one sensor is simply substituted for another. A drawback of this system is that the patient must wear the device which causes inconvenience for the patient.

U.S. Pat. No. 5,469,139 issued to Ko on Nov. 12, 1995 discloses a latch and an alarm device for securing a door, and activates an alarm if an excess force on the door is detected. A panic switch on the device in case of an emergency also activates the alarm. The device is powered by a battery means. This device does not have a mechanism to indicate the level of power retained in the battery. As such, it may fail to respond when the battery power goes down. Further, such a device does not detect constant downward force, which would be indicative of a suicide attempt.

U.S. Pat. No. 7,024,823 to Keller on Apr. 11, 2006 teaches a door closure having a sloped top surface. As such, a rope, rolled bed sheet, or other hanging implement will slide off of such a sloped door when weight is applied thereto. However, many doorways need to be completely sealed and thus a door having a sloped top surface is not always practical.

Therefore, there is a need for a device that would detect and indicate an excess weight applied to a door. Such a needed device would be durable and reliable. Further, such a device would help alert people of a suicide attempt, thereby saving lives. Additionally, such a needed device would detect tampering, vandalism or disconnection of any of the components thereof and sound an alarm. Moreover, such a device would be easy to use, manufacture and cost effective. The present invention accomplishes these objectives.

SUMMARY OF THE INVENTION

The present device is a weight alarm system for indicating when an excess weight is applied to a door. The weight alarm system is installed in a pivotally mounted door within a door frame. The weight alarm system comprises an excess weight sensing means fixed to at least one peripheral edge of the door. The excess weight sensing means may include a pressure strip means fixed around at least one portion of the peripheral edge of the door. A channel may be formed into at least the portion of the peripheral edge of the door with the pressure strip.

A hinge means is fixed between the door frame and the door. The hinge means in one embodiment is a piano hinge that includes a load cell means fixed between a fixed structure mount and the peripheral edge of the door, or includes a contact switch for detecting a hanging implement contacting the hinge means. When the hinge means contracts between the peripheral edge of the door and the fixed structure mount, a signaling means is actuated to communicate with a weight alarm.

The fixed structure mount of the hinge means, alternately, may include a well that receives the load cell means fixed to a bottom side thereof. The load cell means is adapted to receive a pressure piston having a pivot bearing fixed to a top surface thereof. The pressure piston retracts to actuate the load cell means when excess weight is applied to the door, or door latch, thereby actuating the signaling means. The weight alarm system constantly monitors for suicide attempt to actuate a nurse call system, for example.

The present invention detects and indicates when an excess weight is applied to a door. Such a device prevents a patient from a suicide attempt and thereby reduces the chances of success. Such a needed device detects tampering, vandalism or disconnection of any of the components of a door through an alarm. Moreover, such a device is easy to use, manufacture and cost effective. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Figure 1:
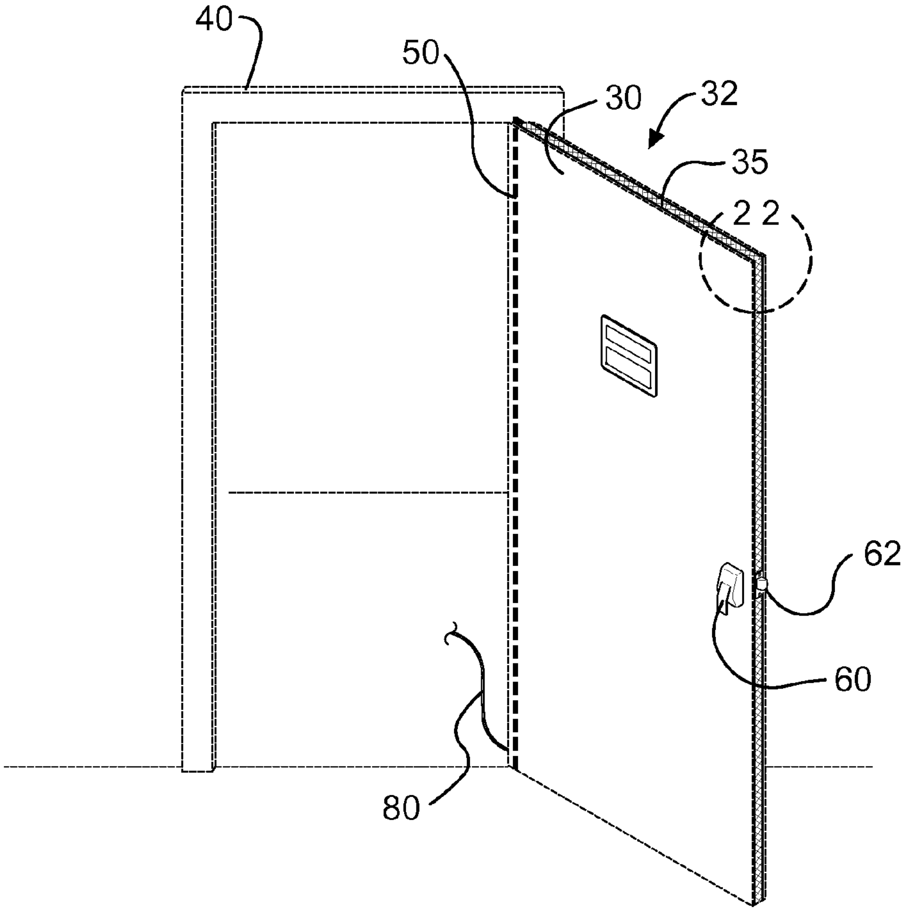
FIG. 1 is a perspective view of one embodiment of the invention.

FIG. 1 illustrates a weight alarm system 10 incorporated into a door 30 and a door frame 40 for indicating when an excess weight 20 is applied to the door 30. The weight alarm system 10 comprises an excess weight sensing means 70 fixed to at least one peripheral edge 35 of the door 30. The excess weight sensing means 70 includes a signaling means 80 for generating a signal when excess weight 20 is detected on the door 30.

The door 30 is pivotally installed within the door frame 40 on at least one hinge means 50. A door latching mechanism 60 traverses either a front side 34 or a rear side 36 of the door 30 having a peripheral edge 35.

Figure 2:
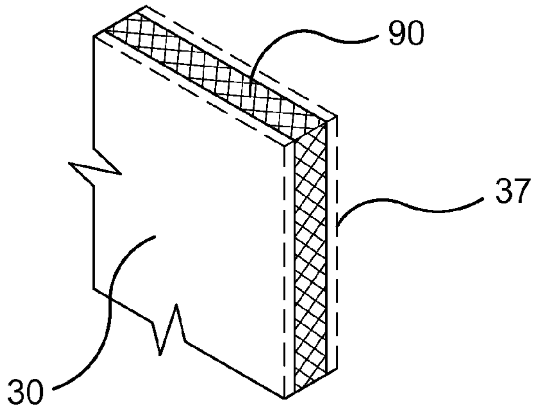
FIG. 2 is a enlarged perspective view of the embodiment of FIG. 1, taken generally along lines 2-2 of FIG. 1, illustrating a pressure strip means fixed around a peripheral edge of a door.
Figure 4:
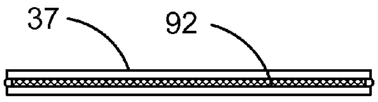
FIG. 4 is a top plan view of the embodiment of FIG. 1, illustrating a portion of a peripheral edge and a portion of the pressure strip means.
Figure 6:
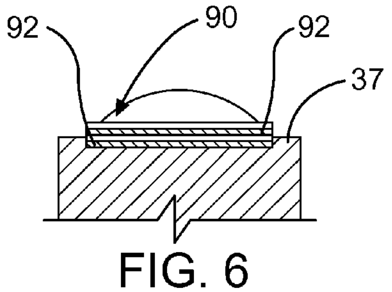
FIG. 6 is an enlarged right-side elevational view of a door taken generally along lines 6-6 of FIG. 5, illustrating a peripheral edge and a pressure strip means of the invention.
Figure 3:
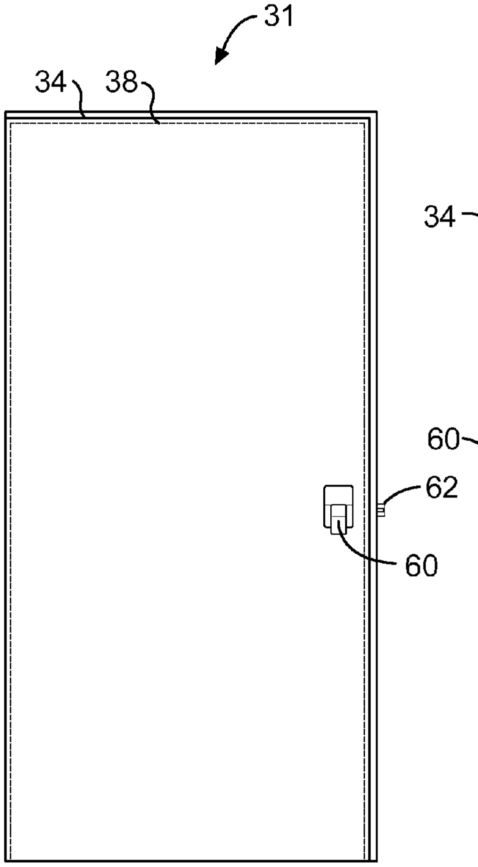
FIG. 3 is a front view of the embodiment of FIG. 1.

The excess weight sensing means 70, in one embodiment, includes a pressure strip means 90, such as a ribbon contact switch, fixed around at least one portion of a peripheral edge 37 of the door 30 (FIG. 6). At least two portions 92 of the pressure strip means 90 are normally urged apart. The two preferably electrically conductive portions 92 of the pressure strip means 90 when forcibly brought into contact actuates the signaling means 80 (FIGS. 2 and 4). The pressure strip means 90 may be made of electrically insulating materials such as soft plastic or rubber, except for the two electrically conductive portions 92. A channel 38 may additionally be formed into at least the portion of the peripheral edge 37 of the door 30 with the pressure strip means 90 (FIGS. 3 and 6). The pressure strip means 90 protrudes partially out of the channel 38.

Figure 11A:
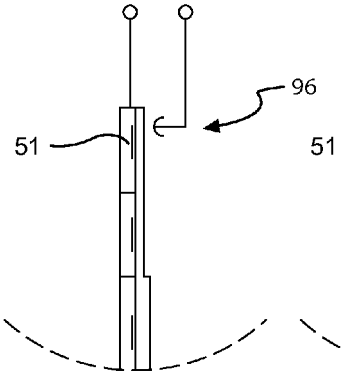
FIG. 11A is an enlarged front elevational diagram of the piano hinge taken generally along lines 11-11 of FIG. 10.
Figure 11B:
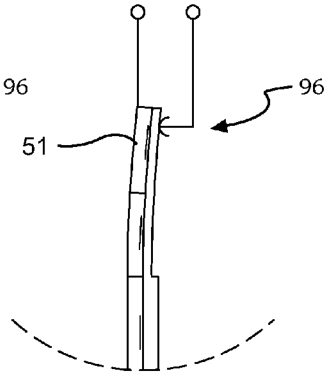
FIG. 11B is an enlarged front elevational diagram of the piano hinge taken generally along lines 11-11 of FIG. 10.
Figure 8:
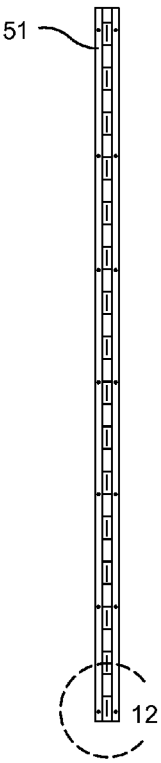
FIG. 8 is a front elevational view of a piano hinge of the invention.
Figure 9:
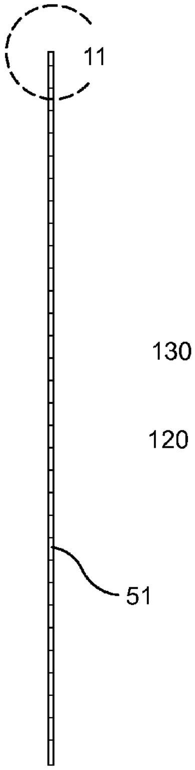
FIG. 9 is a side elevational view of the piano hinge of the invention.
Figure 12:
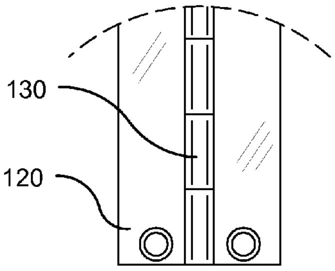
FIG. 12 is an enlarged elevational view of a bottom portion of the piano hinge taken generally along lines 12-12 of FIG. 8 of the invention.
Figure 13:
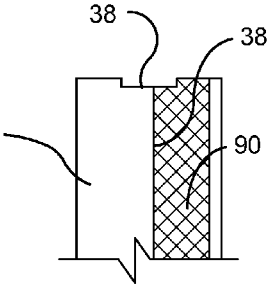
FIG. 13 is an enlarged elevational view of a door, and a channel therein for the pressure strip means of the invention.
Figure 14:
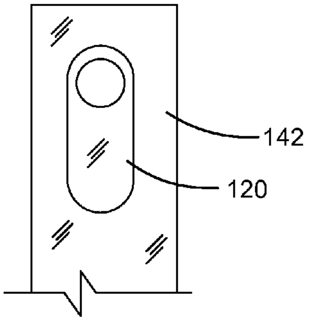
FIG. 14 is an enlarged elevational view of an excess weight sensing means of the invention attached to a bottom peripheral edge of a door.
Figure 15:
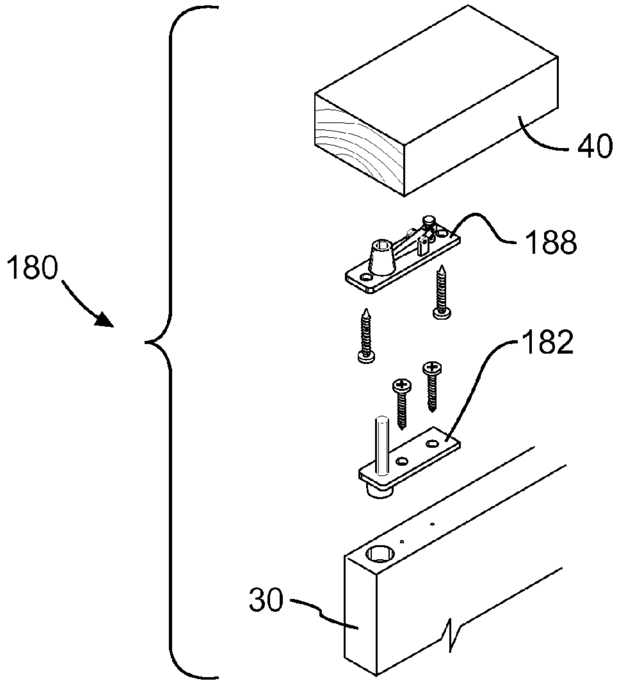
FIG. 15 is an exploded perspective view of an alternate embodiment of the invention, illustrating a top pivot means thereof.

The excess weight sensing means 70, in an alternate embodiment, includes the at least one hinge means 50 fixed to the peripheral edge 35 of the door 30. The hinge means 50 fixed between the door frame 40 and the door 30 may be, for example, a piano hinge 51 that is substantially as tall as the door 30, thereby reducing the ability of a person to secure a hanging implement (not shown) between the door 30 and the door frame 40. The hinge means 50 may be made of stainless or other strong metal continuous piano hinge style (FIGS. 8, 9, 10, 11A and 12). Preferably the pressure strip 90 is included on the peripheral edge 35 of the door 30 adjacent the hinge means 50 to detect if a hanging implement has been pinched between the door frame 40 and the door 30 when the door 30 is closed. Further, a contact switch 96 may be included in the excess weight sensing means 70 and built into a top end of such a piano hinge 51 (FIGS. 11A and 11B), such that any hanging implement proximate thereto will trip close the contact switch 96 and trip the alarm 85. As illustrated, the top portion of the piano hinge 51 is made thinner than the rest of the piano hinge 51 so that under excess weight from a hanging implement the top portion of the hinge 51 will flex towards the contact switch 96. In an alternate embodiment, the contact switch 96 is normally closed, and any hanging implement contacting the contact switch 96 serves to break the circuit to trip the alarm 85. Alternately, the contact switch 96 is a strain gauge (not shown) built into a center post of the hinge 51 that detects excess weight. Alternately, the contact switch 96 may be a standard switch having a rocker arm (not shown) that extends over the hinge 51 so that any hanging implement set onto the contact switch 96 trips the alarm 85. The channel 38 in the door 30 is preferably offset on the vertical sides of the door 30 to allow space for the piano hinge 51 (FIG. 13).

Figure 17:
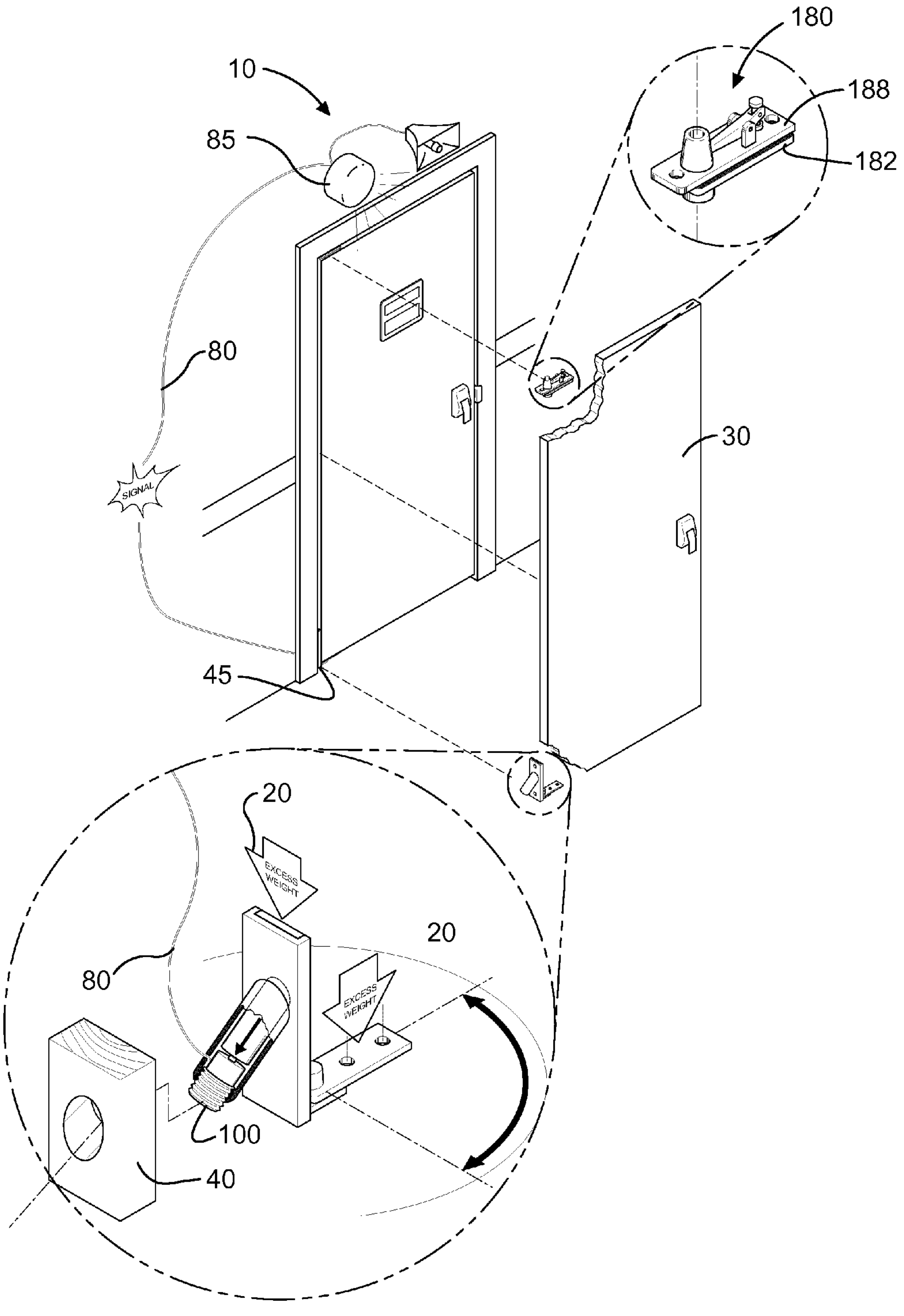
FIG. 17 is a perspective view of the invention in use, illustrating the alternate embodiment of the invention communicating with a weight alarm.
Figure 18:
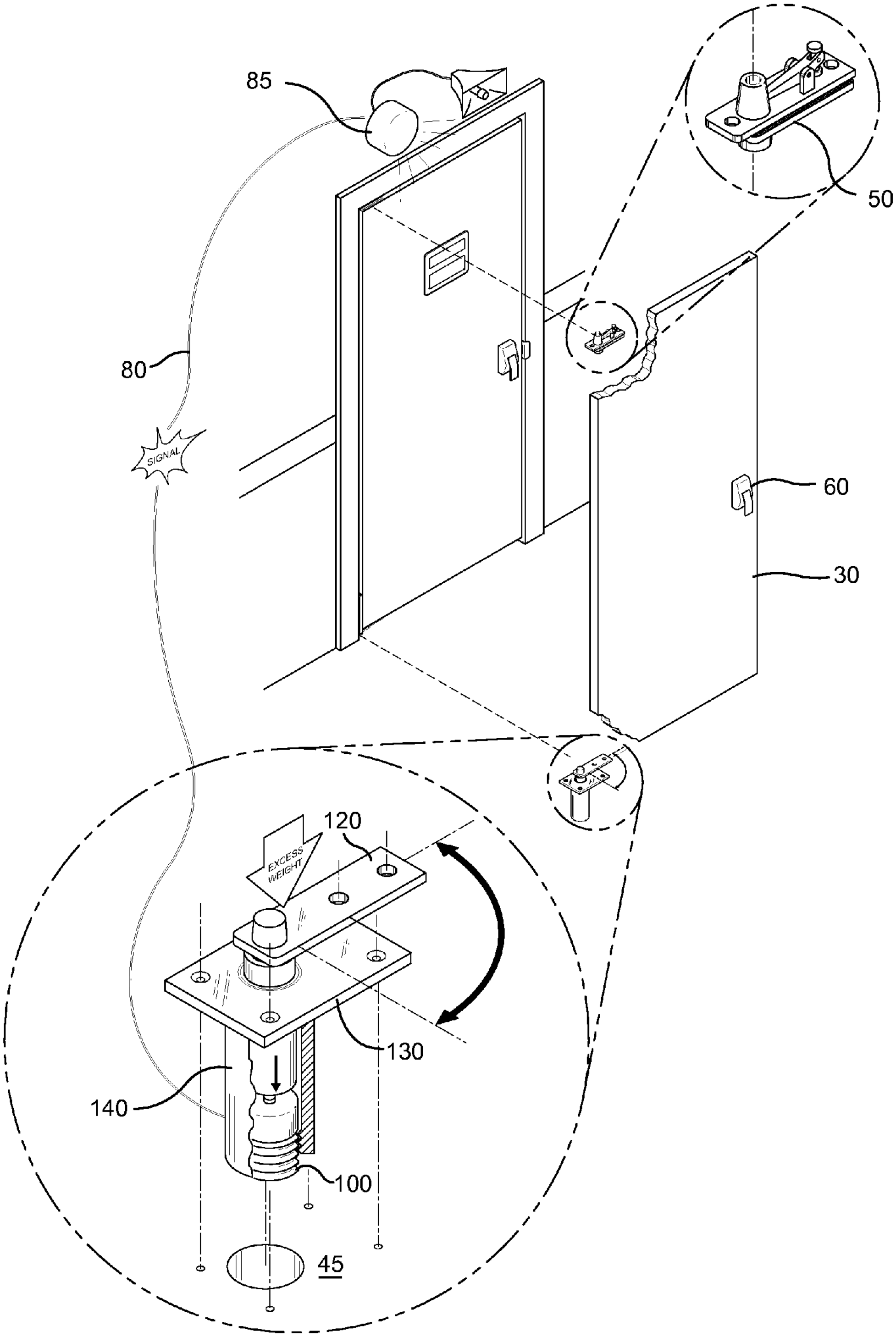
FIG. 18 is an exploded perspective view of another alternate embodiment of the invention.
Figure 19:
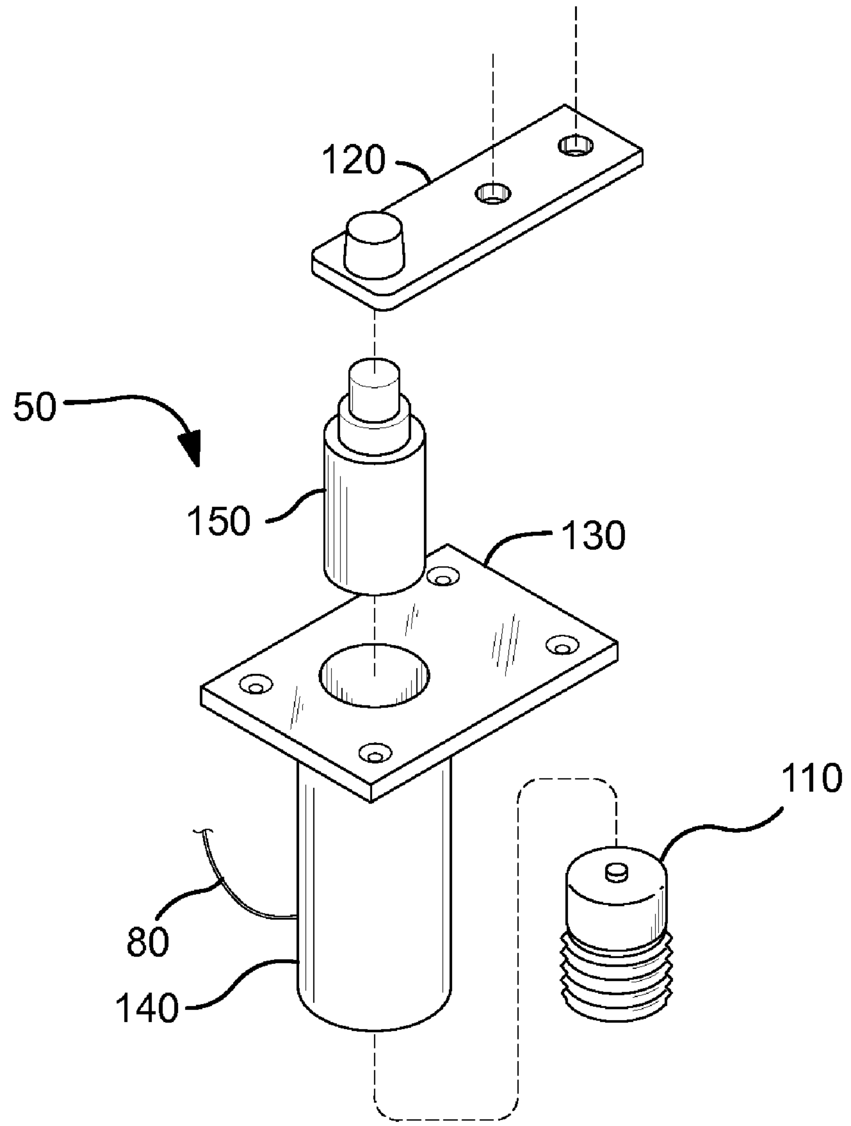
FIG. 19 is a an exploded perspective view of an alternate bottom pivot means of the invention.

The hinge means 50, in an alternate embodiment, includes a load cell means 100 (FIG. 16) fixed between a fixed structure mount 110 and the peripheral edge 35 of the door 30. The fixed structure mount 110 is fixedly attached to the door frame 40. The hinge means 50 contracts between the peripheral edge 35 of the door 30 and the fixed structure mount 110 when excess weight 20 is applied to the door 30. When the hinge means 50 contracts, the signaling means 80 is actuated by the load cell means 100 to communicate with the weight alarm 85, such as a nurse call light system or other alarm. The signaling means 80 may be a flexible cable as illustrated, for example, or a wireless transmitting means (not shown). In another alternate embodiment, the fixed structure mount 110 is fixedly attached to a floor surface 45 adjacent the door frame 40 (FIGS. 18 and 19). An upper pivot means 180 (FIGS. 16 and 17) is also included in such an embodiment, the upper pivot means 180 comprising an upper pivot plate 188 fixed to the door frame and a lower pivot plate 182 fixed to the door and engaging the upper pivot plate 188.

Figure 16:
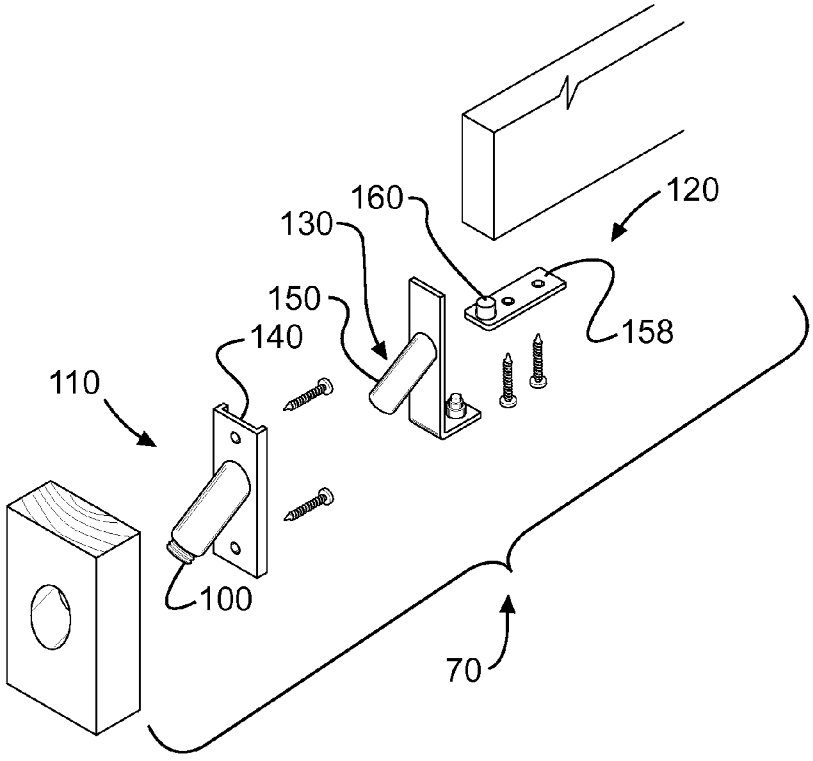
FIG. 16 is an exploded perspective view of the alternate embodiment of the invention, illustrating a bottom pivot means thereof.

In an alternate embodiment, the hinge means 50 has a door pivot bracket 120 pivotally engaging an offset bracket 130 (FIG. 16). The hinge means 50 compresses the load cell means 100 when excess weight 20 is applied to the door 30. The fixed structure mount 110 of the hinge means 50 includes a well 140 that receives the load cell means 100 fixed to a bottom side 142. The load cell means 100 is adapted to receive a pressure piston 150 having a pivot bearing 160 fixed to a top surface 158. The top surface 158 of the pivot bearing 160 pivotally supports the door 30 (FIG. 16). The pressure piston 150 retracts to actuate the load cell means 100 when excess weight 20 is applied to the door 30 thereby actuates the signaling means 80 (FIG. 17).

Figure 5:
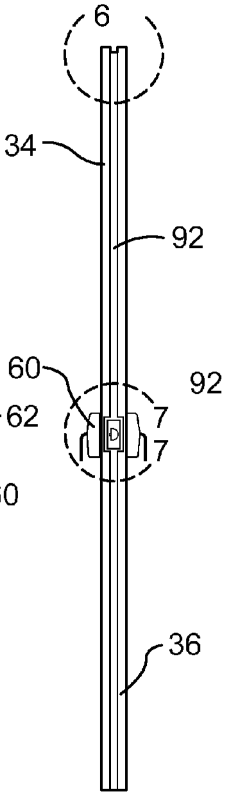
FIG. 5 is a side elevational view of embodiment of FIG. 1, showing the pressure strip means and a door latching mechanism of the invention.
Figure 7:
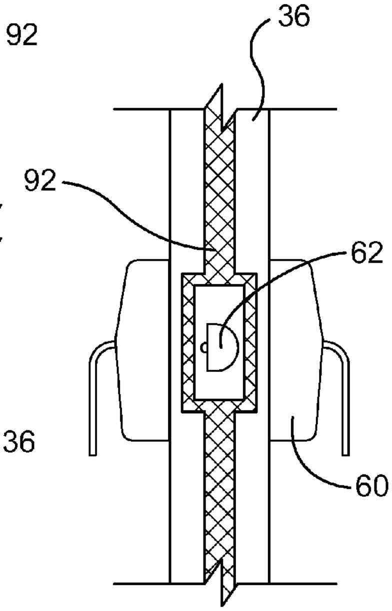
FIG. 7 is a enlarged view of a door latching mechanism taken generally along lines 7-7 of FIG. 5.
Figure 10:
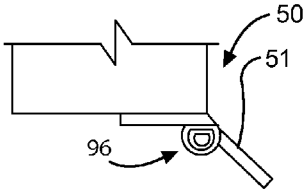
FIG. 10 is an enlarged top plan view of the piano hinge of the invention.

The door latching mechanism 60 is fixed at least partially through the peripheral edge 35 of the door 30 and at least through the front side 34 or the rear side 36 of the door 30. The latching mechanism 60 includes a latching bolt 62 that fixes the door 30 in a closed position 31 within the door frame 40 (FIGS. 5 and 7). Refraction of the latching bolt 62 is actuates the latching mechanism 60 to allow the door 30 to achieve an open position 32 within the door frame 40.

A method for indicating excess weight 20 applied to the door 30 comprises the steps of installation of the weight alarm door system 10 as herein described. The weight alarm door 30 is then attached to the door frame 40. The weight alarm door system 10 then continuously monitors for excess weight, indicative of a suicide attempt, to actuate the weight alarm 85. The signaling means 80 may be electrically normally closed, such that attempts to disable the weight alarm 85 by cutting the signaling means 80 results in activating the alarm means 85.

In the embodiment wherein the door 30 is included as part of the system 10, the door 30 may be constructed in standard sizes of metal or wood to specifications in accordance with building codes. Preferably the pressure strip 90 is included around the door latching mechanism 60 so as to detect pressure caused by a suicide attempt therearound.

While a particular form of the invention has been illustrated and described, it will be apparent that various modifications can be made without departing from the spirit and scope of the invention. For example, the pressure strip means 90 may be made from variety of materials and it may have various modes of operation. Various types of signaling means 80 can be adopted. Also, the excess weight sensing means 70 may be accommodated in different locations of the door 30. In addition, the hinge means 50 and the door 30 may take various design considerations. Accordingly, it is not intended that the invention be limited, except as by the appended claims.

What is claimed is:

1. A weight alarm for indicating excess weight applied to a door, the door pivotally installed within a door frame on at least one hinge means, a door latching mechanism traversing at least either a front or rear side of the door, and a door peripheral edge, the alarm system comprising:

an excess weight sensing means fixed to at least the door at the peripheral edge thereof, the excess weight sensing means including a signaling means for signaling when excess weight is detected on the door, wherein the excess weight sensing means includes the at least one hinge means fixed to the peripheral edge of the door, the hinge means including a load cell means fixed between a fixed structure mount and the peripheral edge of the door, the fixed structure mount fixedly attached to the door frame such that excess weight on the door forces the hinge means to contract between the peripheral edge of the door and the fixed structure mount, actuating the signaling means.

2. The weight alarm of claim 1 wherein the excess weight sensing means comprises a pressure strip means fixed around at least a portion of the peripheral edge of the door, the pressure strip means including at least two portions that are urged apart, and that when forcibly brought into contact are adapted to actuate the signaling means.

3. The weight alarm of claim 2 wherein the door further includes a channel formed into at least the portion of the peripheral edge with the pressure strip means, the pressure strip means protruding at least partially out of the channel.

4. The weight alarm of claim 1 wherein the hinge means further includes a door pivot bracket pivotally engaging an offset bracket that compresses the load cell means when excess weight is applied to the door.

5. A weight alarm for indicating excess weight applied to a door, the door pivotally installed within a door frame on at least one hinge means, a door latching mechanism traversing at least either a front or rear side of the door, and a door peripheral edge, the alarm system comprising:

an excess weight sensing means fixed to at least the door at the peripheral edge thereof, the excess weight sensing means including a signaling means for signaling when excess weight is detected on the door, the excess weight sensing means includes the at least one hinge means fixed to the peripheral edge of the door, the hinge means including a load cell means fixed between a fixed structure mount and the peripheral edge of the door, the fixed structure mount fixedly attached to a floor surface adjacent the door frame such that excess weight on the door forces the hinge means to contract between the peripheral edge of the door and the fixed structure mount, actuating the signaling means.

6. The weight alarm of claim 5 wherein the fixed structure mount of the hinge means includes a well that includes the load cell means fixed to a bottom side thereof, the well adapted to receive a pressure piston having a pivot bearing fixed to a top surface thereof, the top surface of the pivot bearing adapted to pivotally support the door, such that excess weight applied to the door causes the pressure piston to retract to actuate the load cell means, actuating the signaling means.

7. The weight alarm of claim 5 wherein the excess weight sensing means comprises a pressure strip means fixed around at least a portion of the peripheral edge of the door, the pressure strip means including at least two portions that are urged apart, and that when forcibly brought into contact are adapted to actuate the signaling means.

8. The weight alarm of claim 7 wherein the door further includes a channel formed into at least the portion of the peripheral edge with the pressure strip means, the pressure strip means protruding at least partially out of the channel.

9. A weight alarm door system for installation into a door frame, comprising:

a door pivotally installed within the door frame on at least one hinge means, the door including a front side, rear side, and a peripheral edge;

an excess weight sensing means fixed to at least the door at the peripheral edge thereof, the excess weight sensing means including a signaling means for signaling when excess weight is detected on the door, wherein the excess weight sensing means includes the at least one hinge means fixed to the peripheral edge of the door, the hinge means including a load cell means fixed between a fixed structure mount and the peripheral edge of the door, the fixed structure mount fixedly attached to the door frame such that excess weight on the door forces the hinge means to contract between the peripheral edge of the door and the fixed structure mount, actuating the signaling means.

10. The weight alarm door system of claim 9 wherein the excess weight sensing means comprises a pressure strip means fixed around at least a portion of the peripheral edge of the door, the pressure strip means including at least two portions that are urged apart, and that when forcibly brought into contact are adapted to actuate the signaling means.

11. The weight alarm door system of claim 10 wherein the door further includes a channel formed into at least the portion of the peripheral edge with the pressure strip means, the pressure strip means protruding at least partially out of the channel.

12. The weight alarm door system of claim 9 wherein the hinge means further includes a door pivot bracket pivotally engaging an offset bracket that compresses the load cell means when excess weight is applied to the door.

13. A weight alarm door system for installation into a door frame, comprising:

a door pivotally installed within the door frame on at least one hinge means, the door including a front side, rear side, and a peripheral edge;

an excess weight sensing means fixed to at least the door at the peripheral edge thereof, the excess weight sensing means including a signaling means for signaling when excess weight is detected on the door, wherein the excess weight sensing means includes the at least one hinge means fixed to the peripheral edge of the door, the hinge means including a load cell means fixed between a fixed structure mount and the peripheral edge of the door, the fixed structure mount fixedly attached to a floor surface adjacent the door frame such that excess weight on the door forces the hinge means to contract between the peripheral edge of the door and the fixed structure mount, actuating the signaling means.

14. The weight alarm door system of claim 13 wherein the fixed structure mount of the hinge means includes a well that includes the load cell means fixed to a bottom side thereof, the well adapted to receive a pressure piston having a pivot bearing fixed to a top surface thereof, the top surface of the pivot bearing adapted to pivotally support the door, such that excess weight applied to the door causes the pressure piston to retract to actuate the load cell means, actuating the signaling means.

15. The weight alarm door system of claim 13 wherein the at least one hinge means includes one piano hinge that is substantially as tall as the door and fixed between the door frame and the door.

16. The weight alarm door system of claim 13 wherein the excess weight sensing means comprises a pressure strip means fixed around at least a portion of the peripheral edge of the door, the pressure strip means including at least two portions that are urged apart, and that when forcibly brought into contact are adapted to actuate the signaling means.

17. The weight alarm door system of claim 16 wherein the door further includes a channel formed into at least the portion of the peripheral edge with the pressure strip means, the pressure strip means protruding at least partially out of the channel.

* * * * *